United States Patent [19]

Yoshida et al.

[11] 4,243,601

[45] Jan. 6, 1981

[54] CYANO SUBSTITUTED DIPHENOQUINONES AND A PROCESS FOR PREPARING THEM

[75] Inventors: Zen-ichi Yoshida; Shigeo Yoneda, both of Kyoto; Hideki Murata, Hachiouji; Yutaka Yasuda, Nagaoka; Saburo Nagakura, Musashino, all of Japan

[73] Assignees: Ajinomoto Company Incorporated, Tokyo; Zen-Ichi Yoshida, Kyoto, both of Japan

[21] Appl. No.: 18,261

[22] Filed: Mar. 7, 1979

[30] Foreign Application Priority Data

Jul. 12, 1978 [JP] Japan .................................. 53-84761

[51] Int. Cl.[3] .................... C07C 120/00; C07C 121/48

[52] U.S. Cl. ............................... 260/396 N; 252/500; 260/465 F; 549/35; 568/643; 568/403

[58] Field of Search .................................... 260/396 N

[56] References Cited

U.S. PATENT DOCUMENTS 3,526,497 9/1970 Obreiter ........................... 260/396 N

OTHER PUBLICATIONS

Cotton et al., Basic Organic Chemistry, 1976, pp. 282–283.

Chem. Abstracts, 54:12064g.

Chem. Abstracts, 60:2849b.

*Primary Examiner*—Vivian Garner

*Attorney, Agent, or Firm*—Oblon, Fisher, Spivak, McClelland & Maier

[57] ABSTRACT

Novel cyano substituted diphenoquinones of the formula,

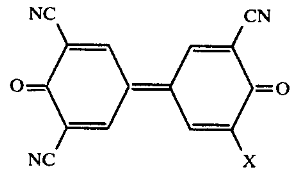

wherein X is a bromine atom or a cyano group, are useful as oxidizing agents and electron acceptors in charge-transfer complex formation owing to their high redox potentials. They may be easily prepared by oxidizing the corresponding cyano substituted biphenols with dinitrogen tetraoxide in an inert organic solvent.

6 Claims, No Drawings

CYANO SUBSTITUTED DIPHENOQUINONES AND A PROCESS FOR PREPARING THEM

BACKGROUND OF THE INVENTION

The present invention relates to novel cyano substituted diphenoquinones which are useful as oxidizing agents and electron acceptors in charge-transfer complex formation and to a process for preparing them.

Charge-transfer complexes are well-known to be utilized as electron materials in the electrophotography and electrostatic record fields. As the representative complex, there is known one composed of the electron acceptor tetracyanoquinodimethane (TCNQ) and the electron-donor tetrathiafulvalene (TTF). The phenomenon of high electrical conductivity of $1.47\times10^{4}\Omega^{-1}cm^{-1}$ at 66° K. in this complex was reported by D. O. Cowan et al in 1973 (J. Am. Chem. Soc., 95, 948–949 (1973) and has aroused intense interest.

It is also known that the electrical conductivity of the charge-transfer complex is greatly dependent on the electron-acceptor, especially it is closely related to the molecular structure (flatness and symmetry), electron-transfer power (redox potential) and large transfer integral (size of molecule) of the electron acceptor.

We have engaged in studies on the syntheses and electronic structures of diphenoquinones substituted by electron-withdrawing groups and previously reported that 2,2',6,6'-tetrachloro or tetrabromodiphenoquinone and 2,6'-dicyano-2',6-dibromodiphenoquinone are useful as electron acceptors because of their higher redox potentials in comparison with the generally employed electron acceptors such as chloranil and TCNQ (see, Abstracts 10th Synposium on Structural Organic Chemistry, pages 164–167 (1977)).

SUMMARY OF THE INVENTION

We have now succeeded in synthesizing novel cyano substituted diphenoquinones of the general formula

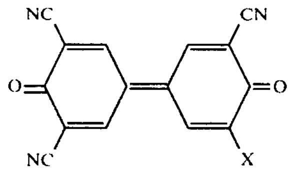

wherein X is a bromine atom or a cyano group and found that cyano substituted diphenoquinones are powerful oxidizing agents and excellent electron acceptors because they have very high redox potentials in comparison with not only generally used electron acceptors such as chloranil, dichlorodicyano-p-benzoquinone (DDQ) and TCNQ but also the homoloque diphenoquinones developed previously by us, as is apparent from comparison tests shown hereafter.

DESCRIPTION OF THE PREFERRED EMBODIMENTS

The novel cyano substituted diphenoquinones of the above formula may be easily prepared by oxidation of the corresponding substituted biphenols of the formula (I)

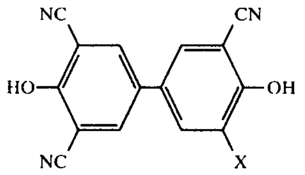

(I)

wherein X has the same meaning as above, with dinitrogen tetraoxide in an inert organic solvent.

In general, the preparation of halogen or dicyanodibromo substituted diphenoquinones may be accomplished by oxidation of the corresponding substituted biphenol with lead tetraacetate. However, when the oxidation of tricyanomonobromo- or tetracyanobiphenol of the above formula (I) has been carried out with lead tetraacetate, no reaction has occurred. Contrary thereto, the oxidation of the raw materials of the formula (I) to the desired diphenoquinones may be efficiently achieved only by use of dinitrogen tetraoxide which is a radical oxidizing agent.

In carrying out the process of the present invention, the raw material cyano substituted biphenol is dissolved or suspended in an inert organic solvent. While the resultant solution or suspension is maintained at temperatures ranging from about −10° C. to about 10° C., preferably at around 0° C., dinitrogen tetraoxide is added in proportions of 5 to 20 times volume per weight of the raw material. Usually, the time required for the completion of the reaction is 1 to 8 hours. Preferred solvents are carbon tetrachloride and hexachloroethane.

After the reaction has been completed, the product crystallizes out and is isolated from the reaction mixture by filtration. If necessary, it may be further purified by recrystallization from a suitable solvent, e.g. acetone-petroleum ether mixed solvent.

The novel cyano substituted diphenoquinones of the present invention form a complex with an equimolar amount of tetrathiafulvalene and hence it may also be isolated as the complex from the reaction mixture.

The property of the product of the present invention as a powerful oxidizing agent is supported by a fact that oxidation of isopropyl alcohol by it affords acetone, while isopropyl alcohol is not oxidized at all with dichlorodicyano-p-benzoquinone which is known as an oxidizing agent for conversion of allyl alcohol into an $\alpha,\beta$- unsaturated ketone.

The cyano substituted biphenols for use as raw materials in the present process are novel substances and may be prepared by the following method.

3,3',5,5'-tetrabromobiphenol is acetylated with acetic anhydride to produce 3,3',5,5'-tetrabromobiphenodiacetate which is subjected to the Rosenmund-Braun reaction for substitution of bromine atoms by cyano groups to form a mixture of 3,3',5-tricyano-5'-bromobiphenodiacetate and 3,3',5,5'-tetracyanobiphenodiacetate, which are separated by thin layer chromatography and hydrolyzed with an aqueous alkaline solution, whereby 3,3',5-tricyano-5'-bromobiphenol and 3,3',5,5'-tetracyanobiphenol are prepared.

The present invention is further illustrated by the following examples.

EXAMPLE 1

Preparation of 2,2',6-tricyano-6'-bromodiphenoquinone

100 Mg of 3,3',5-tricyano-5'-bromobiphenol was placed in a 100 ml flask and suspended in 30 ml of carbon tetrachloride. 1 Ml of dinitrogen tetraoxide was added thereto and the mixture was cooled to 0° C. with the aid of an ice-water bath and stirred for 4 hours.

The precipitated purplish red solid was filtered, washed with carbon tetrachloride and reprecipitated from acetone-petroleum ether mixture to yield 80 mg of purplish red crystalline, 2,2',6-tricyano-6'-bromodiphenoquinone. Yield 80%. M.P. above 360° C.

| | |
|---|---|
| IR spectrum (KBr) | 1635 $cm^{-1}$ (C=C)<br>2240 $cm^{-1}$ (C≡N) |
| UV spectrum | λ max nm |
| Acetonitrile | 423 |
| Acetone | 427 |
| Methylene chloride | 435 |

EXAMPLE 2

Preparation of 2,2',6,6'-tetracyanodiphenoquinone

The procedure of Example 1 was repeated except that 100 mg of 3,3',5,5'-tetracyanobiphenol was employed in place of 100 mg of 3,3',5-tricyano-5'-bromobiphenol. There was obtained 75 mg of purple crystals of 2,2',6,6'-tetracyanodiphenoquinone. Yield 75%. M.P. above 360° C.

| | |
|---|---|
| IR spectrum | 1640 $cm^{-1}$ (C=O)<br>2240 $cm^{-1}$ |
| UV spectrum | λ max nm |
| Acetonitrile | 425 |
| Acetone | 427 |
| Methylene chloride | 430 |

EXAMPLE 3

Preparation of cyano substituted diphenoquinone tetrathiafulvalene (TTF) complex 0.005 Mole of tetrathiafulvalene and 0.005 mole of cyano substituted diphenoquinone obtained by Example 1 or 2 were dissolved in acetonitrile solvent separately and combined. The color of the solution turned to bluish green from yellow and dark purple crystals precipitated, were filtered and dried.

The melting points of the obtained complexes and the characteristic absorption band in their IR spectrum were as follows.

| | M.P. (°C.) | IR spectrum ($cm^{-1}$) |
|---|---|---|
| TTF-2,2',6-tricyano-6'-bromodiphenoquinone | 168–170 | 1605 |
| TTF-2,2',6,6'-tetracyanodiphenoquinone | 187–189 | 1610 |

Measurement of Redox Potential

The redox potentials (E ½) of the cyano substituted diphenoquinones of Examples 1 and 2 were measured using a rotating platinum electrode.

The concentration of test compound in dry acetonitrile solvent was $0.2\times10^{-3}$ to $0.5\times10^{-3}$ mole per liter of solvent. The redox potential was measured by polarography using 0.1 N tetraethylammonium perchlorate as supporting salt. Also, Ag/AgBr electrode was employed as the standard electrode and the measurement was conducted between −0.5 V and 1.0 V.

The results of measurement regarding the redox potential are shown in the following table which also shows the results obtained when a similar test was conducted with respect to the known electron acceptors chloranil, dichlorodicyano-p-benzoquinone (DDQ), tetracyanoquinodimethane (TCNQ), diphenoquinone, 2,2',6,6'-tetrachlorodiphenoquinone, 2,2',6,6'-tetrabromodiphenoquinone and 2,6'-dicyano-2',6-dibromodiphenoquinone for the purpose of comparison.

TABLE

Redox Potentials of Quinones

| | Compound | Redox potential (volt) |
|---|---|---|
| Control | Diphenoquinone | −0.09(−0.30) |
| | 2,2',6,6'-Tetrachlorodiphenoquinone | +0.29(−0.01) |
| | 2,2',6,6'-Tetrabromodiphenoquinone | +0.24(−0.04) |
| | 2,6'-Dicyano-2',6-dibromodiphenoquinone | +0.48(+0.17) |
| | Chloranil | +0.14 |
| | DDQ | +0.38 |
| | TCNQ | +0.08 |
| The present invention | 2,2',6-Tricyano-6'-bromodiphenoquinone | +0.66(+0.46) |
| | 2,2',6,6'-Tetracyanodiphenoquinone | +0.82(+0.54) |

Note:
Numerical values in parenthesis indicate the second stage of redox potentials.

As is apparent from the above table, the cyano substituted diphenoquinones of the present invention are excellent as electron acceptors because of their higher redox potentials than any of the known electron acceptors.

Oxidation of Isopropyl Alcohol 30 mg (0.00011 mole) of 2,2',6,6'-tetracyanodiphenoquinone was added to 0.1 ml (0.0021 mole) of isopropyl alcohol and refluxed whereby purple crystals of 2,2',6,6'-tetracyanodiphenoquinone were converted into white crystals of 3,3',5,5'-tetracyanobiphenol. Also, the formation of acetone as the oxidation product of isopropyl alcohol was observed by gas chromatography.

On the other hand, oxidation of isopropyl alcohol with DDQ or TCNQ under similar conditions gave no acetone.

REFERENTIAL EXAMPLE 1

Preparation of 3,3',5-tricyano-5'-bromobiphenol

30 G of 3,3',5,5'-tetrabromobiphenodiacetate and 30 g of copper cyanide were placed in a 100 ml flask and 250 ml of N,N-dimethylformamide was added thereto. The mixture was refluxed for 2.5 hours under an atmosphere of argon and then 60 g of ferric chloride, 30 ml of hydrochloric acid and 170 ml of water were added and heated at 60°–70° C. for 20 minutes under stirring.

The reaction mixture was extracted with 300 ml of benzene and the benzene layer was treated with an active carbon and filtered. The filtrate was twice washed with 200 ml of water and the benzene layer was dried over anhydrous sodium sulfate and subjected to silicagel column chromatography eluting with methylene chloride to yield 3,3',5-tricyano-5'-bromobiphenodiacetate having a melting point of 270° C.

800 Mg of tricyanomonobromobiphenodiacetate obtained thus was dissolved in 50 ml of methanol and a solution of 450 mg of potassium hydroxide in 50 ml of water was added thereto, and then heated at 70°–80° C. for 1 hour under stirring. Diluted hydrochloric acid was added until the solution was acidified whereupon white solid precipitated, was filtered and dissolved in acetone. After removal of potassium chloride by filtration, acetone was distilled to yield 3,3′,5-tricyano-5′-bromobiphenol, which was recrystallized from ethanol-water. The purified crystals had a melting point of 297°–300° C.

REFERENTIAL EXAMPLE 2

Preparation of 3,3′,5,5′-tetracyanobiphenol

50 G of 3,3′,5,5′-tetrabromobiphenol and 30 ml of ethanol were placed in a 1 l four necked flask and a solution of 15 g of sodium hydroxide in 300 ml of water was dropwise added from a dropping funnel. And then, 50 ml of dimethylsulfuric acid was dropwise added thereto from a dropping funnel and heated at 70°–80° C. for 3 hours under stirring, whereupon white solid was formed and filtered out. The filtrate was extracted with 500 ml of benzene and then with 300 ml of water.

The benzene layer was dried over anhydrous sodium sulfate and concentrated to distill benzene. The residue was recrystallized from methylene chloride-petroleum ether to yield 38 g of white crystals of 3,3′,5,5′-tetrabromobiphenodianisole having a melting point of 211°–212° C.

10 G of the tetrabromobiphenodianisole obtained thus and 10 g of copper cyanide were placed in a 300 ml flask and 100 ml of N,N-dimethylformamide was added. The mixture was heated at reflux temperature for 3 hours under an atmosphere of argon. And then, 20 g of ferric chloride, 10 ml of hydrochloric acid and 60 ml of water were added thereto and heated at 60°–70° C. for 20 minutes with stirring.

The reaction mixture was subjected to silicagel column chromatography eluting with benzene to yield 3,3′,5,5′-tetracyanobiphenodianisole having a melting point of 283°–285° C.

To 500 mg of 3,3′,5,5′-tetracyanobiphenodianisole were added 300 mg of anhydrous aluminum chloride and 200 mg of sodium chloride and then heated at 180° C. for 25 minutes under stirring. After cooling to room temperature, black solid was pulverized and boiled in 100 ml of water. The resultant aqueous solution was extracted with ether three times and then with 2 N aqueous sodium hydroxide solution. The aqueous layer was neutralized with hydrochloric acid and the white solid which precipitated was filtered out and then recrystallized from ethanol-water to yield 80 mg of 3,3′,5,5′-tetracyanobiphenol having a melting point of above 360° C.

What we claim is:

1. A compound of the formula

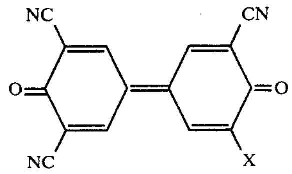

wherein X is a bromine atom or a cyano group.

2. The compound according to claim 1, which is 2,2′,6-tricyano-6′-bromodiphenoquinone.

3. The compound according to claim 1, which is 2,2′,6,6′-tetracyanodiphenoquinone.

4. A process for preparing a cyano substituted diphenoquinone of the formula:

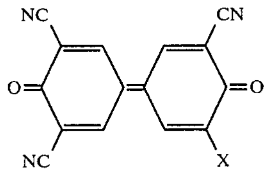

(I)

wherein X is a bromine atom or a cyano group, which comprises: oxidizing a cyano substituted biphenol of the formula:

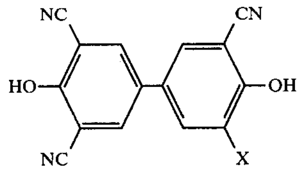

(II)

wherein X is as defined above with from 5 to 20 times the volumes of dinitrogen tetroxide per unit weight of biphenol in an inert organic solvent at a temperature of −10° C. to 10° C.

5. A process according to claim 4, wherein said cyano substituted biphenol is 3,3′,5,5′-tetracyanobiphenol.

6. A process according to claim 4, wherein said inert organic solvent is carbon tetrachloride or hexachloroethane.

* * * * *